US006407206B1

(12) United States Patent
Hayashi et al.

(10) Patent No.: US 6,407,206 B1
(45) Date of Patent: Jun. 18, 2002

(54) PEPTIDES, METHODS FOR ASSAYING HUMAN PEPSINOGEN I OR HUMAN PEPSIN I AND ASSAY KITS

(75) Inventors: Akio Hayashi; Masayoshi Matsuo, both of Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/319,863

(22) PCT Filed: Dec. 10, 1997

(86) PCT No.: PCT/JP97/04540

§ 371 (c)(1),
(2), (4) Date: Jun. 14, 1999

(87) PCT Pub. No.: WO98/25952

PCT Pub. Date: Jun. 18, 1998

(30) Foreign Application Priority Data

Dec. 12, 1996 (JP) ................................ 8-351807

(51) Int. Cl.$^7$ .............................. C07K 7/06; C12Q 1/37
(52) U.S. Cl. .................... 530/329; 530/330; 435/23; 435/24
(58) Field of Search ................. 530/329, 330; 435/23, 24, 213, 212, 226

(56) References Cited

U.S. PATENT DOCUMENTS 5,879,897 A * 3/1999 Koufman

FOREIGN PATENT DOCUMENTS

| CS | 261172 | 6/1989 | ............ C12Q/1/38 |
| JP | 61-260899 | 11/1986 | ............ C12Q/1/36 |

OTHER PUBLICATIONS

Baxter, Allan et al, Substrate and Inhibitor Studies with Human Gastric Aspartic Proteinases, Biochem. J., vol. 267, No. 3, pp. 665–669, (1990).
Rao, Chetana M. et al, Specificity in the Binding of Inhibitors to the Active Site of Human/Primate Aspartic Proteinase: Analysis of $P_2-P_1-P_1,-P_2,$ Variation, J. Med. Chem. (1993), 36, pp. 2614–2620.
Filippova, Irina Y. et al, Fluorogenic Peptide Substrates for Assay of Aspartyl Proteinases, Analytical Biochemistry 234, pp. 113–118 (1986).
Chiang, L. et al, The Separate Determination of Human Pepsin and Gastricsin, Proc. Soc. Exp. Biol. Med., (1966), 122, pp. 700–704.
Lehninger Biochemistry Copyright@1975 by Worth Publishers, Inc. chapter 21.*
Grabner et al. Plasma gastrin and gastric secretory response to duodenal perfusion with liver extract in healthy human subjects. Scand j Gastroenterol, 1977 recd 1978 12 7, 865–868.*
Jablonowski et al. The activity of digestive enzymes and the stomach acidity in weaning piglets feeding with hydrochloric acid acidified diet. Med Weter, 1991 47 9, 423–424.*
Roth et al. Determination of pancreatic carboxypeptidase A in human blood serum Clinica Chimica Acta, 135 1983 65–71 Elsevier.*
Vercaigne–Marko In vivo and in vitro Inhibition of Human Pancreatic Chymotrypsin A by Serum Inhibitors Biol. Chem Hoppe–Seyler vol. 368 pp. 37–45 Jan. 1987.*
Mahler et al., Biological Chemistry, 2nd edition. p. 117. Harper & Row, Publishers, New York. 1971.*
Tang, J. "Gacstricin and pepsin" in Methods in Enzymology. vol. 19, pp. 406–421. 1970.*

* cited by examiner

*Primary Examiner*—Michael P. Woodward
*Assistant Examiner*—Marjorie A Moran
(74) *Attorney, Agent, or Firm*—Sughrue Mion, PLLC

(57) ABSTRACT

Peptide substrates, or acid addition salts thereof, wherein said peptide substrate is represented by formula (I):

R-X-Pro-Ile-Glu-W-Y-Z     (I)

wherein R is a hydrogen, an amino-protective group, or a residue carrying one or two D- or L-amino acids; X is Lys or Arg; W is Phe or Phe(NO$_2$), wherein Phe(NO$_2$) is p-nitrophenylalanine; Y is Phe, Phe(NO$_2$), Tyr, 3,5-diiodotyrosine, norleucine, Leu, Asp(Osbzl) or Met, wherein Obzl is benzyloxy; and Z is an aniline, an aminocoumarin or an aminonapthalene derivative, are disclosed. These compounds are specific substrates for human pepsin I and are useful in assaying the presence of human pepsin I or human pepsinogen I, and useful in diagnosing gastric diseases, such as gastric cancer and gastric ulcer.

5 Claims, 1 Drawing Sheet

Figure
The correlation between Invention method and RIA method
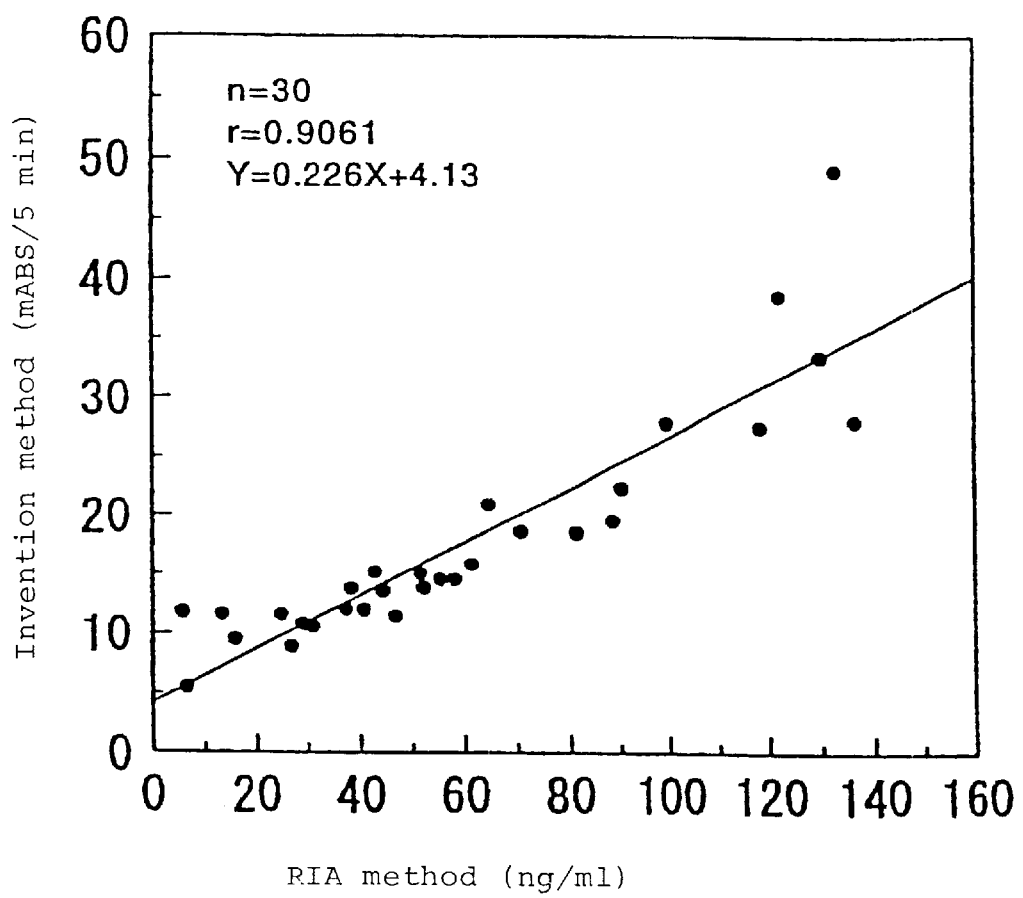

PEPTIDES, METHODS FOR ASSAYING HUMAN PEPSINOGEN I OR HUMAN PEPSIN I AND ASSAY KITS

This application is the National Stage filing under 35 U.S.C. §371 of PCT/JP97/04540 filed Dec. 10, 1997.

FIELD OF THE INVENTION

The present invention relates to a method for assaying human pepsinogen I or human pepsin I in the human body fluid (such as gastric juice, blood, urine etc.) as diagnostic marker of gastric diseases such as gastric cancer, gastric ulcer etc., and a peptide used as substrate in such a method.

More detailed, the present invention relates to
(1) a peptide of the formula (I)

R-X-ProIleGlu-W-Y-Z   (I)

(wherein R is hydrogen, an amino-protective group, or a residue containing one or two D-amino acid or L-amino acid, X is Lys or Arg residue, W is Phe or Phe(NO$_2$) residue (in which Phe(NO$_2$) is p-nitrophenylalanine residue.), Y is Phe, Phe(NO$_2$), Tyr, Dit, Nle, Leu, Asp(OBzl) or Met residue (in which Dit is 3,5-diiodotyrosine residue, Nle is norleucine residue, OBzl is benzyloxy and Phe(NO$_2$) is as defined hereinbefore.), and Z is an aniline derivative residue, an aminocoumarine derivative residue or an aminonaphthalene derivative residue.), or an acid addition salt thereof and, (2) a method for assaying human pepsinogen I or human pepsin I which is characterized by digesting a peptide of the said formula (I) or an acid addition salt thereof by human pepsin I which is obtained by activation of human pepsinogen I in a sample or human pepsin I in a sample to obtain an amino acid derivative of the formula (II)

H-Y-Z   (II)

(wherein all the symbols are as defined.), digesting the obtained amino acid derivative by aminopeptidase to obtain an aniline, aminocoumarine or aminonaphthalene derivative of the formula Z-H and then detecting the obtained aniline, aminocoumarine or aminonaphthalene derivative.

BACKGROUND

It is known that the pepsinogen secretion is parallel to gastric acid secretion and that human serum or urine pepsinogen levels is also parallel to gastric pepsinogen secretion. The above pepsinogen exists as pepsinogen in the body fluid such as blood or urine except for gastric juice, on the other hand, it exists as pepsin in gastric juice. It is said that the blood or urine pepsinogen I level of the patient with atrophic gastritis decreases and that human blood pepsinogen I and pepsinogen II levels increase in case of gastric ulcer. In addition, the level of pepsinogen I is said to decrease in the patient with gastric cancer (Japanese Patent Application Kokai Hei 7-304800). Therefor, a assaying the level of human pepsinogen I in human blood or urine may be useful for diagnosis of gastric diseases such as gastric cancer, gastric ulcer etc. in early stage.

As for a method for assaying human pepsin which was obtained by activation of human pepsinogen, a method using human serum protein etc. in urine and serum based on its digesting activity has been known (Clin. Chem., 15, 1, 42–55 (1969)). The significance of clinical trial using such a method has been discussed, but it requires a long time. In addition, its accuracy was not good, so such a method has been of no practical use. Further, the results means the activity to digest protein, so it was reflected on the total activities of both pepsin I and pepsin II. Therefore it is impossible to determine the human serum pepsinogen I specifically.

Recently, a method for assaying human pepsinogen in urine (uropepsin) indirectly, based on inactivation of an aciduric enzyme by activated pepsin was proposed (Japanese Patent Application Kokai Hei 7-155198). But the substrate used in this method did not show the specificity for pepsin I. It is said that the pepsinogen in urine is pepsinogen I. But, pepsin II may be also secreted in urine in some body condition, so it is difficult to determine the accurate level of pepsin I. It is impossible to assay the level of pepsinogen I in human serum specifically.

As for a method for assaying pepsinogen I, radio immunoassay (Gastroenterology, 66, 494 (1974)) and enzyme immunoassay (Japanese Patent Application Kokai Hei 7-304800) using a specific anti-body have been practical use, but these methods cause a radioactive pollution and require a long time and complicated procedure for determination.

As for a method for assay using synthesized substrate, for example, it was described that a peptide of the formula (A-1)

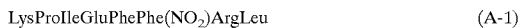

LysProIleGluPhePhe(NO$_2$)ArgLeu   (A-1)

(wherein Phe(NO$_2$) is as defined hereinbefore.) was used as substrate in assaying inhibitory effect of some compounds on human pepsin I in the paper of J. Med., Chem., 36, 2614 (1993). That is to say, a peptide of the formula (A-1) was digested by human pepsin I to obtain a peptide of the formula (A-2)

Phe(NO$_2$)ArgLeu   (A-2)

(wherein Phe(NO$_2$) is as defined hereinbefore,)
and the obtained peptide of the formula (A-2) was used in the assaying inhibitory activity on enzyme based on decrease of absorbance at 234~324 nm as an index.

But this paper did not disclose that such a peptide of the formula (A-1) may be as a substrate for human pepsin I. Therefore, it is uncertain whether this peptide has a specificity for human pepsin I, or not. In addition, the chromophore of this peptide is Phe(NO$_2$), so it is expected that the accuracy of the method using this peptide is one tenth or less to compare with p-nitroaniline (abbreviated as pNA). Further, it is impossible to be used in automated clinical analyzer due to detection at 234~324 nm.

In CS-261172, a peptide of the formula (B-1)

X-A-B-Phe-D-pNA   (B-1)

(wherein X is hydrogen, C3~5 carboxylalkylcarbonyl or C1~5 alkylcarbonyl,

A is pyroglutamic acid (abbreviated as pGlu), Asp, Glu or Gly residue or 2-oxoimidazoline-1-yl-carbonyl, B is His, Gly or Pro residue, D is Phe, Leu, Nle, Met or S-C1~3 alkyl-Cys residue, and pNA is p-nitroaniline residue.)

was used as a substrate in assaying activities of pepsin I, pepsin II and chymosin.

But, there was neither description nor suggestion about the specificity of this peptide for human pepsin I.

In the example, a peptide of the formula (B-2)

pGluHisPhePhe-pNA (B-2)

(wherein pGlu and pNA are as defined hereinbefore.)
was used in assaying activity of pig pepsin. This pig pepsin was not purified and thought to be an mixture of pepsin I and pepsin II. So, it is not expected that this substrate possesses a specificity for human pepsin I.

There is a common part in chemical structure between these substrates described in the above two references (J. Med. Chem., 36, 2614 (1993) and CS-261172) and the substrate of the present invention, but these compounds are distinct from this substrate in total chemical structure. There are neither description nor suggestion that the peptides of the present invention have a specificity for human pepsin I in these references.

In addition, in the paper of Anal. Biochem., 234, 113 (1996), a peptide of the formula (C-1)

Abz-AlaAlaPhePheAlaAla-Ded (C-1)

(wherein Abz is o-aminobenzoyl and Ded is N-2,4-dinitrophenylethylenediamine.),
or a peptide of the formula (C-2)

Abz-AlaAlaPhePheAlaAla-pNA (C-2)

(wherein Abz and pNA are as defined hereinbefore.)
were used as substrate in assaying activities of human pepsin I, human pepsin II, human cathepsin D and HIV protease by fluorophotometry.

In this paper, the fluorescent changes caused by modification of peptide was discussed. Particularly, a peptide of the formula (C-1) seemed to be suggested to have specificity for human pepsin I from the experimental result. But, the level of specificity is insufficient. A peptide of the formula (C-1) was distinct from a peptide of the present invention in structure. Therefore, it is not expected that the peptide of the present invention has the specificity for human pepsin I from the peptide of the reference.

Further, in the paper of Proc. Soc. Exp. Biol. Med., 122, 700 (1966), a peptide of the formula (D-1)

Ac-Phe-Dit (D-1)

(wherein Ac is acetyl and Dit is 3,5-diiodotyrosine residue.)
was used as a substrate in specifically assaying human pepsin I. But this method required a long time and complicated procedure. This method is of no practical use due to the above reason and low accuracy and low sensitivity.

A peptide of the formula (D-1) was distinct from a peptide of the present invention in structure. Therefore, it is not expected that the peptide of the present invention has the specificity for human pepsin I from the peptide of the reference.

DISCLOSURE OF THE INVENTION

The present inventors have been studying to dissolve these problems of the related arts and to find a substrate which is high-sensitive (being high rate of enzyme reaction i.e., digesting a substrate by human pepsin I at a high rate and/or being able to produce efficient coloring) and specific for human pepsin I, and then have succeeded in synthesizing a substrate (peptide) which is sensitive and specific for human pepsin I. By using this substrate, it become to possible to determine pepsin I for short time to compare with the method of related arts and to determine pepsinogen I using automated clinical analyzer.

That is to say, the present invention relates to
1) a peptide of the formula (I)

R-X-ProIleGlu-W-Y-Z (I)

(wherein R is hydrogen, an amino-protective group, or a residue containing one or two D-amino acid or L-amino acid, X is Lys or Arg residue, W is Phe or Phe(NO$_2$) residue (in which Phe(NO$_2$) is p-nitrophenylalanine residue.), Y is Phe, Phe(NO$_2$), Tyr, Dit, Nle, Leu, Asp(OBzl) or Met residue (in which Dit is 3,5-diiodotyrosine residue, Nle is norleucine residue, OBzl is benzyloxy and Phe(NO$_2$) is as defined hereinbefore.), and Z is an aniline derivative residue, an aminocoumarine derivative residue or an aminonaphthalene derivative residue.), or an acid addition salt thereof,
2) a peptide described in the above 1), wherein Y is Phe, Phe(NO$_2$), Tyr or Nle residue wherein all the symbols are as defined in the above 1),
3) a peptide described in the above 1) or 2), wherein R is hydrogen or C1~6 alkylcarbonyl,
4) a peptide of the formula (Ia)

N$^\alpha$-Ac-LysProIleGluPheNle-pNA (Ia)

(wherein Ac is acetyl, Nle is norleucine residue, pNA is p-nitroaniline residue.),
a peptide of the formula (Ib)

LysProIleGluPheNle-pNA (Ib)

(wherein all the symbols are as defined hereinbefore.),
a peptide of the formula (Ic)

LysProIleGluPheTyr-pNA (Ic)

(wherein all the symbols are as defined hereinbefore.),
a peptide of the formula (Id)

LysProIleGluPhePhe-pNA (Id)

(wherein all the symbols are as defined hereinbefore.),
a peptide of the formula (Ie)

LysProIleGluPhePhe(NO$_2$)pNA (Ie)

(wherein Phe(NO$_2$) is p-nitrophenylalanine residue, and the other symbol is as defined hereinbefore.),
or a peptide of peptide of the formula (If)

N$^\alpha$-AcLysProIleGluPhe(NO$_2$)-NlepNA (If)

(wherein all the symbols are as defined hereinbefore.), or acid addition salts thereof, 5) a method for assaying human pepsinogen I or human pepsin I characterized by
digesting a peptide of the formula (I) described in the above 1)
(wherein all the symbols are as defined in the above 1).), or an acid addition salt thereof, by human pepsin I which is obtained by activation of human pepsinogen I in a sample or human pepsin I in a sample to obtain an amino acid derivative of the formula (II)

$$H\text{-}Y\text{-}Z \qquad (II)$$

(wherein all the symbols are as defined in the above 1).),
digesting the obtained amino acid derivative by aminopeptidase to obtain an aniline, aminocoumarine or aminonaphthalene derivative of the formula Z-H and then detecting the obtained aniline, aminocoumarine or aminonaphthalene derivative,
6) a method for assaying described in the above 5) using a peptide of the formula (Ia), (Ib), (Ic), (Id), (Ie) or (If) wherein all the symbols are as defined in the above 4) or an acid addition salt thereof,
7) a kit for assaying human pepsinogen I or human pepsin I which is characterized by comprising a peptide of the formula (I) (wherein all the symbols are as defined in the above 1).), or an acid addition salt thereof as a substrate and aminopeptidase.

BRIEF EXPLANATION OF FIGURE

FIG. 1 shows correlation between a conventional method for assaying serum pepsinogen I (RIA) using a kit for assaying pepsinogen I (Dinabott Co), and a method for assaying of the present invention.

DETAILED EXPLANATION OF THE INVENTION

The present invention relates to,
(1) a peptide of the formula (I)

$$R\text{-}X\text{-}ProIleGlu\text{-}W\text{-}Y\text{-}Z \qquad (I)$$

(wherein all the symbols are as defined hereinbefore.), or an acid addition salt thereof,
(2) a method for assaying human pepsinogen I or human pepsin I characterized by digesting a peptide of the formula (I) depicted in the above (1) (wherein all the symbols are as defined hereinbefore), or an acid addition salt thereof by human pepsin I which is obtained by activation of human pepsinogen I in a sample or human pepsin I in a sample to obtain an amino acid derivative of the formula H-Y-Z (wherein all the symbols are as defined hereinbefore), digesting the obtained amino acid derivative to obtain an aniline, aminocoumarine or aminonaphthalene derivative of the formula Z-H, and then detecting the obtained aniline, aminocoumarine or aminonaphthalene derivative, and
(3) a kit for assaying human pepsinogen I or human pepsin I which is characterized by comprising a peptide of the formula (I) depicted in the above (1) or an acid addition salt thereof as a substrate, and aminopeptidase.

A sample as objet in the present invention means any sample to be determined the concentration of human pepsinogen I and activity of human pepsin I. For example, such a sample includes human body fluid (such as gastric juice, blood or urine etc.). The above pepsinogen exists as form of pepsinogen in the body fluid such as blood or urine except for gastric juice, on the other hand, it exists as form of pepsin in gastric juice.

The abbreviation consisting of three characters in a peptide of the formula (I), (Ia), (Ib), (Ic), (Id), (Ie) or (If) and in the paragraph of background means amino acid well known and its definition is as follows:
Pro=proline,
Ile=isoleucine,
Glu=glutamic acid,
Phe=phenylalanine,
Lys=lysine,
Arg=arginine,
Tyr=tyrosine,
Leu=leucine,
Asp=aspartic acid,
Met=methionine,
Gly=glycine,
His=histidine,
Cys=cystein,
Ala=alanine.

As for the abbreviation consisting three characters other than above, Dit is 3,5-diiodotyrosine, Nle is norleucine (in which, side chain of leucine is a straight butyl).

Unless otherwise specified, an amino acid in the peptide of the present invention means L-amino acid except for D-amino acid or L-amino acid represented by R.

The peptide of the present invention may be converted into the corresponding acid additional salts. Water-soluble salts are preferable. Suitable acid addition salts, for example, are salts of inorganic acids, e.g., such as hydrochloric acid, hydrobromic acid, phosphonate, sulphonate, nitric acid etc., or salts of organic acids, e.g., succinate, citrate, lactate, malate, benzenesulfonate, acetate, trifluoroacetate etc. Trifluoroacetate is preferable.

An aniline, aminocoumarine or aminonaphthalene derivative represented by Z-H means unsubstituted aniline, unsubstituted aminocoumarin, and unsubstituted aminonaphthalene or substituted ones wherein benzene ring, coumarin ring, naphthalene ring in each group is substituted by 1~5 of substituent(s) selected from the group consisting of nitro, amino, amino gourd substituted by one or two C1~6 alkyl, C1~6 hydroxyalkylamino, carboxyl, hydroxy, halogen, C1~6 alkyl, C1~6 alkoxy, thiol, sulfonyl, C1~6 alkylsulfonyl, —CH$_2$CH$_2$COOH and —CH═CH—COOH. Preferably, the number of such substituent(s) is 1, 2 or 3.

Aniline derivative represented by Z-H includes, for example, p-nitroaniline, m-anisidine, 3,5-dibromo-4-hydroxyaniline, N',N'-diethyl-phenylenediamine or 3-carboxyl-4-hydroxyaniline.

Aminocoumarine derivative or aminonaphthalene derivative represented by Z-H includes, for example, 7-amino-4-methylcoumarin, 4-methyl-2-aminonaphthalene, 4-methoxy-2-aminonaphthalene.

Preferably, group represented by Z-H includes, for example, p-nitroaniline, m-anisidine, 7-amino-4-methylcoumarin, 4-methyl-2-aminonaphthalene, 4-methoxy-2-aminonaphthalene. More preferably, it includes p-nitroaniline or m-anisidine.

An amino-protective group represented by R includes, for example, C1~6 alkylcarbonyl, C1~6 alkylsulfonyl, benzyloxycarbonyl, tert-butoxycarbonyl, 9-fluorenylmethoxycarbonyl or benzoyl or its derivative wherein benzene ring in benzyloxycarbonyl or benzoyl is unsubstituted or by 1~5 of substituent(s) selected from the group consisting of nitro, amino, amino gourd substituted by one or two C1~6 alkyl, C1~6 hydroxyalkylamino, carboxyl, hydroxy, halogen, C1~6 alkyl, C1~6 alkoxy, thiol, sulfonyl, C1~16 alkylsulfonyl, —CH$_2$CH$_2$COOH and —CH═CH—COOH).

In the above C1~6 alkylcarbonyl, C1~6 alkylsulfonyl and substituent and substituent attached to aniline of Z, C1~6 alkyl means methyl, ethyl, propyl, butyl, pentyl or hexyl, or isomer thereof.

A residue containing one or two D-amino acid or L-amino acid represented by R is an α-amino-protective group in Lys or Arg residue represented by X. Preferably, R means hydrogen or C1~6 alkylcarbonyl, more preferably, hydrogen or acetyl.

X is Lys or Arg residue which is a basic amino acid, preferably, Lys residue.

W is Phe or Phe($NO_2$) residue which is an aromatic amino acid, preferably, Phe residue.

Y is Phe, Phe($NO_2$), Tyr or Dit residue which is an aromatic amino acid, or Nle, Leu, Asp(OBzl) or Met residue which is an aliphatic amino acid, preferably, Phe, Phe($NO_2$), Tyr or Nle residue and more preferably Nle residue.

A peptide (substrate) of the present invention includes, for example, a peptide of the formula (Ia), (Ib), (Ic), (Id), (Ie) or (If), preferably, peptide of the formula (Ia).

Process for Preparing Peptides of the Present Invention

A peptide used as a substrate in the present invention may be prepared by the well-known methods in chemical synthesis of peptide. For example, a peptide of the present invention may be prepared by reacting an aniline, aminocoumarine or aminonaphthalene derivative of the formula Z-H as chromophore with an amino acid of the formula $Ra^1$-Y-OH (wherein $Ra^1$ is an amino-protective group and the other symbol is as defined hereinbefore), and coupling the obtained compound with an amino acid successively as shown in Reaction Scheme 1 hereinafter, or by coupling a few amino acids each other to obtain a few kind of polypeptides and then coupling such a few kind of polypeptides successively as shown in Reaction Scheme 1 or Examples hereinafter.

or two D-amino acid or L-amino acid and the other symbols are as defined hereinbefore.)

In the above coupling or reaction, amino and carboxyl group which does not relate the reaction is protected by a protective group used ordinary in synthesizing a peptide. An amino-protective group represented by $Ra^1$~$Ra^9$ includes, for example, benzyloxycarbonyl (CBZ), tert-butoxycarbonyl (Boc) or 9-fluorenylmethoxycarbonyl (Fmoc) etc. When an Arg or Lys is used in reaction, a δ-guanidino and ε-amino group in Arg and Lys, respectively, is protected by a protective group. A carboxyl-protective group represented by Rc includes, for example, ester group such as benzyl or tert-butyl ester etc. When Glu is used in reaction, the carboxyl group in the side chain is protected by a protective group. Each protective group is removable by the known method after reaction.

The coupling reaction of chromophore and amino acid may be carried out by the methods known per se, for example, (1) by the method using acid halide
(2) by the method using mixed acid anhydride
(3) by the method using conducing agent (EDC, PyBrop, DCC etc.)

Concrete description of the methods described above are as follows:

(1) method using acid halide may be carried out, for example, amino acid in which an amino group is protected (for example, amino acid of the formula $Ra^1$-Y-OH, $Ra^2$-W-OH etc.) is reacted with an acid halide (oxalyl chloride or thionyl chloride etc.) in an organic solvent (chloroform, methylene chloride, diethylether or THF (tetrahydrofuran) etc.) or without solvents at from −20° C. to a refluxing temperature of the solvent used to give an acid halide. The obtained acid halide and an aniline, aminocoumarine or aminonaphthalene derivative of the formula Z-H or a (poly) peptide in which an amino-protective group is removed

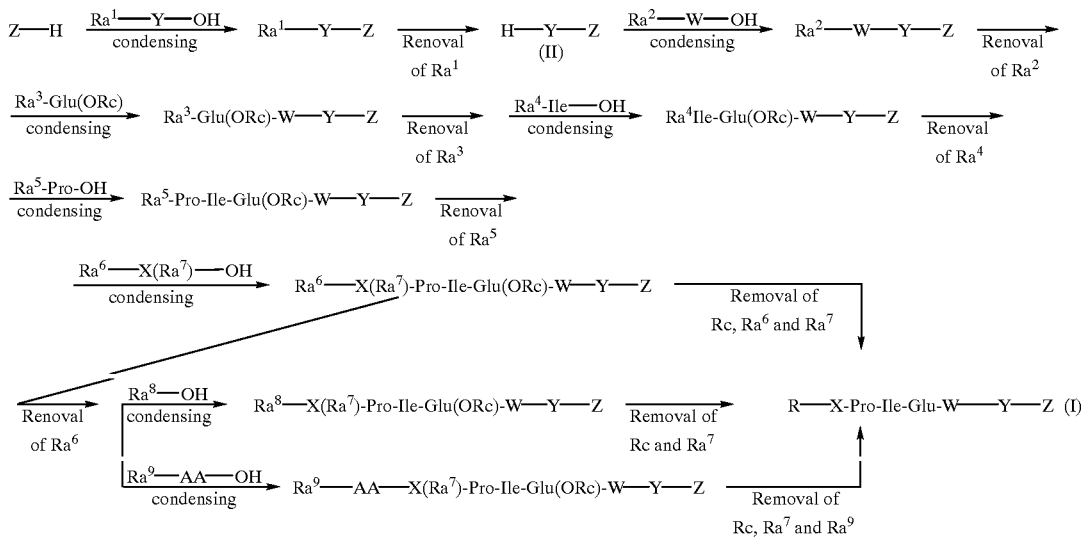

Reaction Scheme 1

(wherein each $Ra^1$~$Ra^9$ is an amino-protective group, Rc is a carboxyl-protective group, AA is a residue containing one (for example, (poly)peptide of the formula H-Y-Z, H-W-Y-Z etc.) are reacted in an organic solvent (chloroform, methylene chloride, diethylether, THF etc.) in the presence of tertiary amine (pyridine, triethylamine, dimethylaniline, dimethylaminopyridine, diisopropylethylamine etc.) at 0~40° C.

(2) method using mixed acid anhydride may be carried out, for example, amino acid in which the amino group is protected (for example, amino acid of the formula $Ra^1$-Y-OH, $Ra^2$-W-OH etc.) is reacted with an acid halide (pivaloyl chloride, tosyl chloride, mesyl chloride etc.) or an acid derivative (ethyl chloroformate, isobutyl chloroformate etc.) in an organic solvent (chloroform, methylene chloride, diethyl ether, THF etc.) or without solvents, in the presence of tertiary amine (pyridine, triethylamine, dimethylaniline or dimethylaminopyridine etc.) at 0~40° C. to give mixed acid anhydride. The obtained mixed acid anhydride and an aniline, aminocoumarine or aminonaphthalene derivative of the formula Z-H or a (poly)peptide in which an amino-protective group is removed (for example, (poly)peptide of the formula H-Y-Z, H-W-Y-Z etc.) are reacted in an organic solvent (chloroform, methylene chloride, diethylether, THF etc.) at 0~70° C.

(3) method using condensing agent such as EDC (1-(3-dimethylaminopropyl)-3-ethylcarbodiimido), PyBrop (bromo-tris-pyrolydino-phosphoniumuhexafluorophosphate), DCC (dicyclohexylcarbodiimido) etc. may be carried out, for example; amino acid in which an amino group is protected (for example, amino acid of the formula $Ra^1$-Y-OH, $Ra^2$-W-OH etc.) and an aniline, aminocoumarine or aminonaphthalene derivative of the formula Z-H or a (poly)peptide in which an amino-protective group is removed (for example, (poly)peptide of the formula H-Y-Z, H-W-Y-Z etc.) are reacted in an organic solvent (chloroform, methylene chloride, diethylether or THF etc.) or without solvents in the presence or absence of tertiary amine (pyridine, triethylamine, dimethylaniline, dimethylaminopyridine, diisopropylethylamine etc.) using with EDC, PyBrop or DCC etc. at 0~40° C.

Preferably, the reactions (1), (2) and (3) described above are carried out under an atmosphere of inert gas (argon, nitrogen, etc.) on anhydrous condition.

Removal of a protective group may be carried out by the known method. For example, removal of CBZ or Bzl may be carried out under the atmosphere of hydrogen gas, in an organic solvent (methanol, ethanol or THF etc.) by using catalyst (Pd-C, Pd or Ni etc.) at 0~50° C. Removal of Boc may be carried out in a water-miscible organic solvent (methanol, ethanol, THF or dioxane etc.) by using organic acid (acetic acid, p-toluene sulfonic acid, trifluoro acetic acid or trichloro acetic acid etc.) or inorganic acid (hydrochloric acid or hydrobromic acid etc.) at 0~90° C. Removal of both Boc and Bzl at the same time may be carried out in the presence of thioanisole, m-chlezole etc. in trifloromethane sulfonic acid+trifluoro acetic acid or hydrogen fluoride.

In each reaction in the present specification, obtained products may be purified by conventional techniques. For example, purification may be carried out by distillation at atmospheric or reduced pressure, by high performance liquid chromatography, by thin layer chromatography or by column chromatography using silica gel or magnesium silicate, by washing or by recrystallization. Purification may be carried out after each reaction, or after a series of reactions.

A peptide of the formula (I) may be converted into a corresponding acid addition salt thereof by the known method.

[Starting Materials and Reagents]

The starting materials and reagents in the present invention are known or may be prepared by known methods.

[The Method for Assay]

The enzymatic reaction used in the method for assaying of the present invention is shown in Reaction Scheme 2.

Reaction Scheme 2

Enzymatic Reaction (1) First Reaction human pepsinogen I

Activation human pepsin I

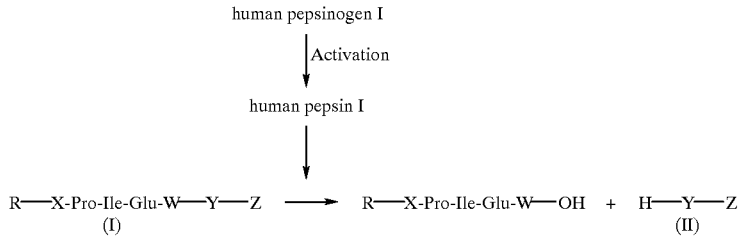

(2) Second Reaction aminopeptidase

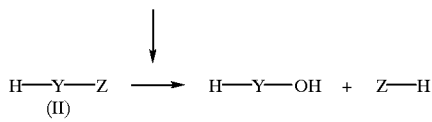

(wherein all the symbols are as defined hereinbefore.)

As for a sample, in the case of body fluid except for gastric juice such as blood, urine etc., human pepsinogen I is activated to human pepsin I in the First Reaction, and the obtained human pepsin I recognizes and digests a peptide of the formula (I) (wherein all the symbols are as defined hereinbefore), or an acid addition salt thereof as a substrate, specifically. This activation of human pepsinogen I may be carried out, for example, under ail acidic condition in combination with digesting a substrate at the same time or separately. As for this acidic condition, pH 1.0~6.0 is preferable. A buffer includes tartaric acid, glycine, citric acid, oxalic acid, formic acid, acetic acid preferably. An amino acid derivative of the formula (II) H—Y—Z (wherein all the symbols are as defined hereinbefore), which is released after the digesting reaction is digested by aminopeptidase (for example, aminopeptidase M derived from pig kidney) at pH 6~9 to give an aniline, aminocoumarine or aminonaphthalene derivative of the formula Z-H in the Second Reaction. It is possible to assay human pepsinogen I in a sample by detecting the obtained aniline, aminocoumarine or aminonaphthalene derivative.

On the other hand, in the case of gastric juice, human pepsin I recognizes and digests a peptide of the formula (I) (wherein all the symbols are as defined hereinbefore), or an acid addition salt thereof as a substrate under an acidic condition in the First Reaction specifically. As for this acidic condition, pH 1.0~6.0 is preferable. A buffer includes tartaric acid, glycine, citric acid, oxalic acid, formic acid, acetic acid buffer preferably. An amino acid derivative of the formula (II) which is released after the digesting reaction is digested similarly to give an aniline, aminocoumarine or aminonaphthalene derivative. It is possible to assay human pepsin I in a sample by detecting the obtained aniline, aminocoumarine or aminonaphthalene derivative.

The detecting an aniline derivative may be carried out by the assaying the increase in absorbance of aniline derivative itself or by the assaying corresponding adequate coloring agent. An aniline derivative may be converted into a corresponding adequate coloring agent by reacting the said aniline derivative under an acidic condition to give diazo chromophore. The concrete material for diazo-coupling includes 3,5-xylenol, N-ethyl-N-(2-hydroxy-3-sulfopropyl)-3,5-dimethylaniline or its salt (MAOS) etc. Such a converting may be carried out by addition of metal kilate complex such as pentacyanoamine feroate etc. or by oxidizing and condensing a phenol derivative, aniline derivative or xylenol derivative etc.

The detecting an aminocoumarine derivative, aminonaphthalene derivative is carried out by fluorometery (for example, $\lambda$ex=380 nm, $\lambda$em=460 nm on 7-amino-4-methylcoumarin; $\lambda$ex=335 nm, $\lambda$em=410 nm on 4-methyl-2-aminonaphthalene).

INDUSTRIAL AVAILABILITY

A peptide of the formula (I) or an acid addition salt thereof of the present invention is a substrate possessing the specificity for human pepsin I and high sensitivity (digesting a substrate by pepsin I at a high rate and/or being able to produce efficient coloring). Therefore, a method for assaying human pepsin I or human pepsinogen I by using a peptide or an acid addition salt thereof of the present invention is useful for diagnosis of gastric diseases such as gastric cancer, gastric ulcer etc. and contributes to the clinical field.

EXAMPLES

The following examples are intended to illustrate, but not limit, the present invention. The thin layer chromatographic separations were carried out by using the following developing or eluting solvents. The solvents in parentheses of NMR show solvents used in determination. The meaning of abbreviation is as follows:
Cbz=benzyloxycarbonyl,
Boc=tert-butoxycarbonyl,
TFA=frifluoroacetic acid,
AcOEt=ethyl acetate,
THF=tetrahydrofuran,
DMF=N,N-dimethylformamide,
N(Et)$_3$=triethylamine,
EDC=1-(3-dimethylaminopropyl)-3-ethylcaribodiimide,
HOBt=1-hydroxybenzotriazole,
pNA=p-nitroaniline,
CH$_2$Cl$_2$=dichloroethane,
MeOH=metahnol,
Et$_2$O=diethyl ether,
PyBrop=bromo-tris-pyrolydino-phosphoniumuhexafluorophosphate,
TFMSA=trifluoromethanesulfonic acid,
Pac=fenasyl.

Example 1

Synthesis of a Peptide Shown as N$^\alpha$-Ac-LysProIleGluPheNle-pNA.CF$_3$COOH 1 (1): BocNle-pNA To a solution of BocNle-OH (8.0 g) in THF (320 ml), N(Et)$_3$ (4.84 ml) was added. Pivaloylchloride (4.26 ml) was added dropwise thereto at room temperature. The mixture was stirred for 1 hour. To the reaction mixture, pNA (5.73 g) was added. The mixture was reacted at 70° C. for 16 hours. After reaction, THF was distilled off under reduced pressure. The residue was dissolved into AcOEt, extracted, washed by a saturated solution of sodium hydrogen carbonate, 1N HCl, a saturated solution of sodium chloride and dried over an anhydrous magnesium sulfate. The organic layer was filtered and concentrated under reduced pressure. The obtained crude was purified on silica gel chromatography (n-hexane:AcOEt=10:1) to give the title compound (3.01 g) having the following physical data.

Rf=0.64 (n-hexane:AcOEt=2:1).

1 (2): BocIleGlu(OBzl)PheNle-pNA

BocNle-pNA (prepared in 1 (1); 2.96 g) was dissolved into a solution of 4N—HCl in dioxane (30 ml). After stirring the obtained solution for 1 hour at room temperature, dioxane was distilled off under reduced pressure and then by adding toluene (30 ml). The reaction mixture was crystallized in ether to give Nle-pNA.HCl (2.08 g).

BocPhe-OH (2.06 g) and HOBt (1.05 g) were dissolved into anhydrous DMF (40 ml). To the solution, EDC (1.49 g) was added at –10° C. After stirring the mixture for 30 minutes, a solution of Nle-pNA.HCl (2.03 g) which was prepared hereinbefore and N(Et)$_3$ (1.03 ml) in DMF (20 ml) was added dropwise thereto at –10° C. The mixture was reacted at –10° C. for 30 minutes and at room temperature for 16 hours. After reaction, DMF was distilled off under reduced pressure. The residue was dissolved into AcOEt, extracted, washed by a saturated solution of sodium hydrogen carbonate, 1N HCl, a saturated solution of a ammonium chloride, a saturated solution of sodium chloride and dried over an anhydrous magnesium sulfate. The organic layer was filtered and concentrated under reduced pressure. The obtained crystal was washed and filtered to give BocPheNle-pNA 3.37 g (96%).

By the same procedure as above, the obtained compound was reacted to condense with Boc-Glu(OBzl)-OH (2.45 g) and BocIle-OH (1.44 g) successively to give the title compound (2.63 g) having the following physical data.

Rf=0.84 (CHCl$_3$:MeOH=20:1).

1 (3):IleGlu(OBzl)PheNle-pNA.HCl

BocIleGlu(OBzl)PheNle-pNA (prepared in 1 (2); 3.59 g) was dissolved into a solution of 4N—HCl in dioxane (15 ml). After stirring a solution at room temperature for 1 hour, dioxane was distilled off under reduced pressure and then by adding toluene (30 ml). The solution was crystallized in ether to give the title compound (3.38 g).

Rf=0.09 (CHCl$_3$:MeOH=20:1).

1 (4): CbzLys(Boc)Pro(OBzl)

Cbz-Lys(Boc)-OH (7.1 g) and diisopropylethylamine (6.82 ml) were dissolved into CH$_2$Cl$_2$ (40 ml). To the obtained solution, PyBrop (9.14 g) and a solution of Pro (OBzl).HCl (4.73 g, 1.1 eq) and diisopropylethylamine (3.41 ml, 1.1 eq) in CH$_2$Cl$_2$ (5 ml) were added at −10° C. The mixture was reacted for 30 minutes. After reaction, CH$_2$Cl$_2$ was distilled off under reduced pressure. The residue was dissolved into Et$_2$O, extracted, washed by water, an aqueous solution of 10% citric acid, a saturated solution of sodium hydrogen carbonate, dried over an anhydrous magnesium sulfate. The organic layer was filtered and concentrated under reduced pressure. The obtained crude was purified on silica gel chromatography (CHCl$_3$:MeOH=200:1) to give the title compound (7.12 g) having the following physical data.

Rf=0.51 (CHCl$_3$:MeOH=20:1).

1 (5) :Lys(Boc)Pro-OH

In to a solution of Cbz-Lys(Boc)Pro-Obzl (prepared in 1 (4); 3.45 g) and sodium hydrogen carbonate (51 mg) in MeOH (50 ml), 10%Pd-C (400 mg) was added. After reducing under an atmosphere of hydrogen gas at room temperature for 1 hour, the reaction mixture was filtered. The organic layer was concentrated under reduced pressure to give the title compound (2.06 g) having the following physical data.

Rf=0.05 (CHCl$_3$:MeOH=20:1).

1 (6): N$^\alpha$-AcLys(Boc)Pro-OH

Lys(Boc)Pro-OH (prepared in 1 (5); 1.99 g) and 1N—NaOH (10.3 ml) of were dissolved into an aqueous solution of, 50% THF (50 ml) at 0° C. Acetylchloride (0.37 ml) was added dropwise thereto to give the title compound (1.41 g) having the following physical data.

Rf=0.72 (CHCl$_3$:MeOH:AcOH=6:2:1).

1 (7): N$^\alpha$-Ac-Lys(Boc)ProIleGlu(OBzl)-PheNle-pNA

Into a solution of N$^\alpha$-Ac-Lys(Boc)-Pro-OH (prepared in 1 (6); 1.36 g) and HOBt (0.524 g) in anhydrous DMF (20 ml), EDC (0.744 g) was added at −10° C. The reaction mixture was stirred for 30 minutes. A solution of Ile-Glu(OBzl)-PheNle-pNA.HCl (prepared in 1 (3); 2.68 g) and N(Et)$_3$ (0.53 ml) in DMF (15 ml) was added dropwise thereto at −10° C. The mixture was reacted at −10° C. for 30 minutes and at room temperature for 16 hours. After reaction, DMF was distilled off under reduced pressure. The residue was washed by an aqueous solution of 15% citric acid, an aqueous solution of 10% sodium hydrogen carbonate, dissolved into a mixture solvent (CHCl$_3$:MeOH=10:1) and dried over an anhydrous magnesium sulfate. The organic layer was filtered and concentrated under reduced pressure. The obtained crude was purified on silica gel chromatography (CHCl$_3$:MeOH=50:1) to give the title compound (2.97 g) having the following physical data.

Rf=0.39 (CHCl$_3$:MeOH=20:1).

1 (8): N$^\alpha$-Ac-LysProIleGluPheNle-pNA.CF$_3$COOH

N$^\alpha$-Ac-Lys(Boc)-ProIle-Glu(OBzl)-PheNle-pNA (prepared in 1 (7); 0.100 g) was dissolved into a mixture solvent 1M thioanisole.1M TFMSA.TFA (5 ml) containing m-chlezol (0.38 ml) at 0° C. The mixture was stirred for 2 hours to remove a protective group. The reaction mixture was concentrated under reduced pressure and dissolved into TFA (1 ml). The mixture was added dropwise to an iced ether (Et$_2$O) (200 ml). The precipitate was filtered by centrifugation. The residue was washed by iced ether (Et$_2$O) (50 ml) three times and dried under reduced pressure. The obtained crude was dissolved into MeOH. The solution was purified on C18-HPLC-chrom to give the title compound (79 mg) having the following physical data.

$^1$H-NMR: (CD$_3$OD) δ=8.22 (2H, d), 7.88 (2H, d), 7.26 (5H, m), 4.65–4.30 (5H, m), 4.08 (1H, d), 3.95–3.80 (1 H, m), 3.70–3.55 (1H, m), 3.20 (1H, dd), 2.97 (1H, dd), 2.92 (2H, t), 2.38–1.10 (29H, m), 0.98–0.82 (6H, m);

MS: (M+1)m/z=908.

Example 2

Synthesis of a peptide shown as LysProIleGluPheNle-pNA.2CF$_3$COOH 2 (1): CbzPheNle-pNA Into a solution of CbzPhe-OH (94 mg) and HOBt (42 mg) in anhydrous DMF(2 ml), EDC (60 mg) was added at −10° C. The mixture was stirred for 30 minutes. A solution of Nle-pNA.HCl (prepared in process 1 (2); 85 mg) and N(Et)$_3$ (0.040 ml) in DMF (2 ml) was added dropwise thereto at −10° C. The mixture was reacted at −10° C. for 30 minutes and at room temperature for 16 hours. After reaction, DMF was distilled off under reduced pressure. The residue was dissolved into AcOEt, extracted, washed by a saturated solution of sodium hydrogen carbonate, 1N HCl, a saturated solution of ammonium chloride, a saturated solution of sodium chloride and dried over anhydrous magnesium sulfate. The organic layer was filtered and concentrated under reduced pressure. The obtained crystal was washed by water and filtered to give the title compound (109 mg) having the following physical data.

$^1$H-NMR: (d$_6$-DMSO) δ=8.34 (1H, d), 8.22(2H, d), 7.88 (2H, d), 7.50 (1H, d), 7.40–7.10 (10 H, m), 4.95 (2H, s), 4.52–4.30 (2H, m), 3.06 (1H, dd), 2.72 (1H, dd), 1.72 (2H, br m), 1.32 (4H, br s), 0.98 (3H, br m);

MS: (M+1)m/z=533.

2 (2): Boc-Glu(OBzl)-OPac

Boc-Glu(OBzl)-OH (5.0 g) was dissolved into a solution (MeOH: water=9:1) (20 ml). Cesium carbonate (2.41 g) was added thereto at room temperature. The mixture was stirred for 1 hour. The solvent was distilled off under reduced pressure. The obtained crystal was dried under reduced pressure. This crystal was dissolved into DMF (20 ml). Fenasylbromide (2.95 g) was added thereto. After reaction at room temperature for 18 hours, DMF was distilled off under reduced pressure. The residue was dissolved into AcOEt, extracted, washed by an aqueous solution of 5% oxalic acid, a saturated solution of sodium hydrogen carbonate, a saturated solution of sodium chloride, and dried over anhydrous magnesium sulfate. The organic layer was filtered and concentrated under reduced pressure. The obtained crude was crystallized in solvent (n-hexane : AcOEt=1:2) to give the title compound (6.183 g) having the following physical data.

Rf=0.46 (n-hexane :AcOEt=2:1).

2 (3): Cbz-Lys(Cbz)Pro-OtBu

Into a solution of Cbz-Lys(Cbz)-OH (3.00 g), Pro-OtBu (1.36) and N(Et)$_3$ (2.0 ml) in CH$_2$Cl$_2$ (20 ml), a solution of PyBrop (3.37 g) in CH$_2$Cl$_2$ (5 ml) was added dropwise. The mixture was reacted at room temperature for 3.5 hours. After reaction, CH$_2$Cl$_2$ was distilled off under reduced pressure.

The residue was dissolved into AcOEt, extracted, washed by an aqueous solution of 10% oxalic acid, a saturated solution of sodium hydrogen carbonate, a saturated solution of ammonium chloride, a saturated solution of sodium chloride and dried over anhydrous magnesium sulfate. The organic layer was filtered and concentrated under reduced pressure. The obtained crude was purified on silica gel chromatography (n-hexane : AcOEt=1:1) to give the title compound (2.87 g) having the following physical data.

Rf=0.35 (n-hexane :AcOEt=1:1).

2 (4): Cbz-Lys(Cbz)Pro-OH

By the same procedure as described in 1 (2), a protective group of Cbz-Lys(Cbz)Pro-OtBu (prepared in 2 (3); 2.87 g) was removed to give the title compound (1.707 g) having the following physical data.

Rf=0.96 (AcOEt).

2 (5): Cbz-Lys(Cbz)ProIleGlu(OBzl)-OPac

Boc-Glu(OBzl)-Opac (prepared in 2 (2); 3.092 g) was dissolved into dioxane (4 ml). The mixture was reacted to remove a protective group by the same procedure as described in 1 (2) using a solution of 4N—HCl in dioxane. The obtained compound was reacted to condense with BocIle-OH.H$_2$O (1.792 g) by the same procedure as described in 1 (2), additionally, to remove a protective group by the same procedure as described in 1 (2) to give Ile-Glu (OBzl)-OPac.HCl (2.122 g). Into a solution of Cbz-Lys (Cbz)-Pro-OH (prepared in 2 (4); 1.54 g) and HOBt (0.448 g) in anhydrous DMF (10 ml), EDC (0.635 g) was added at −10 ° C. The mixture was stirred for 30 minutes. A solution of IleGlu(OBzl)-OPac.HCl (prepared hereinbefore; 1.551 g) and N(Et)$_3$ (0.45 ml) in DMF (10 ml) was added dropwise thereto at −10° C. The mixture was reacted at −10° C. for 30 minutes and at room temperature for 16 hours. After reaction, DMF was distilled off under reduced pressure. The residue was dissolved into AcOEt, extracted, washed by a saturated solution of sodium hydrogen carbonate, 1N HCl, a saturated solution of ammonium chloride, a saturated solution of sodium chloride and dried over anhydrous magnesium sulfate. The organic layer was filtered and concentrated under reduced pressure. The obtained crude was purified on silica gel chromatography (n-hexane : AcOEt=1:2) to give the title compound (2.542 g) having the following physical data.

Rf=0.58 (AcOEt).

2 (6): Cbz-Lys(Cbz)ProIleGlu(OBzl)-OH

Into a solution of Cbz-Lys(Cbz)ProIleGlu(OBzl)-OPac (prepared in 2 (5); 1.996 g) in acetic acid (20 ml), zinc powder (2.0 g) was added. After reaction at 55° C. for 4 hours, acetic acid was distilled off under reduced pressure. The mixture was dissolved into a solution (10 ml) of 4N—HCl in dioxane. Eter (Et$_2$O) (200 ml) was added thereto to obtain crystal and to give the title compound (1.23 g) having the following physical data.

Rf=0.61 (CHCl$_3$:MeOH :AcOH=80:15:5).

2 (7): Cbz-Lys(Cbz)ProIleGlu(OBzl)PheNle-pNA

A solution of CbzPheNle-pNA (prepared in 2 (1); 51 mg) in 30%HBr-acetic acid was stirred for 30 minutes. The solvent was distilled off under reduced pressure. The reaction mixture was dissolved into anhydrous DMF (2 ml). N(Et)$_3$ (0.013 ml) was added dropwise thereto to obtain PheNle-pNA.Et$_4$NHBr.

Into a solution of Cbz-Lys(Cbz)ProIleGlu(OBzl)-OH (prepared in 2 (6); 80 mg) and HOBt (14 mg) in anhydrous DMF (2 ml), EDC (20 mg) was added at −10° C. The mixture was stirred for 30 minutes. A solution of PheNle-pNA.Et$_4$NHBr (prepared hereinbefore, in DMF was added dropwise thereto at −10° C. The mixture was reacted at −10° C. for 30 minutes and at room temperature for 16 hours. After reaction, DMF was distilled off under reduced pressure. The residue was dissolved into AcOEt, washed by 1N HCl and an aqueous solution of 10% sodium hydrogen carbonate, extracted, washed by a saturated solution of ammonium chloride, a saturated solution of sodium chloride and dried over anhydrous magnesium sulfate. The organic layer was filtered and concentrated under reduced pressure to give the crude of the title compound (106 mg) having the following physical data.

Rf=0.39 (CHCl$_3$:MeOH=20:1).

2 (8) :LysProIleGluPheNlepNA.2CF$_3$COOH

Cbz-Lys(Cbz)ProIleGlu(OBzl)PheNle-pNA (prepared in 2 (7); 106 mg) was dissolved into a mixture solution 1M thioanisol.1M TFMSA. TFA (5 ml) containing m-chlezol (0.38 ml). The mixture was stirred for 2 hours to remove a protective group. The reaction mixture was concentrated under reduced pressure, dissolved into TFA. Iced ether (Et$_2$O) (200 ml) was added dropwise thereto. The precipitate was filtered by centrifugation. The residue was washed by iced ether (Et$_2$O) (50 ml) three times and dried under reduced pressure. The obtained crude was dissolved into MeOH and purified on C18-HPLC-column to give the title compound (17 mg) having the following physical data.

$^1$H-NMR:(CD$_3$OD) δ=8.24 (2H, d), 7.85 (2H, d), 7.26–7.10 (5H, m), 4.64 (1H, dd), 4.55 (1H, dd), 4.42 (1H, dd), 4.38 (1H, dd), 4.25 (1H, dd), 4.11 (1H, d), 3.73 (1H, m), 3.59 (1H, dd), 3.16 (1H, dd), 2.96 (1H, dd), 2.94 (2H, t), 2.36 (2H, t), 2.24 (1H, m), 2.12–1.64 (23H, m), 1.96 (1H, m), 0.96–0.85 (6H, m);

MS: (M+1+18)m/z=884.

Example 3

Synthesis of peptide shown as LysProIleGluPheTyr-pNA.2CF$_3$COOH

By the same procedure as described in Example 2, the title compound having the following physical data was obtained.

$^1$H-NMR:(CD$_3$OD) δ=8.20 (2H, d), 7.79 (2H, d), 7.16 (5H, br s), 7.06 (2H, d), 6.66 (2H, d), 4.57 (3H, m), 4.36 (1H, dd), 4.25 (1H, dd), 4.11 (1H, d), 3.72 (1H, br m), 3.58 (1H, br m), 3.14~2.84 (4H, m), 2.38–1.06 (18H, m), 0.89 (3H, t);

MS: (M+1)m/z=916.

Example 4

Synthesis of peptide shown as LysProIleGluPhePhe-pNA -2CF$_3$COOH

By the same procedure as described in Example 2, the title compound having the following physical data was obtained.

$^1$H-NMR:(CD$_3$OD) δ=8.20 (2H, d), 7.79 (2H, d), 7.30–7.10 (10H, m), 4.75–4.04 (6H, m), 3.78–3.54 (2H, m), 3.20–2.84 (4H, m), 2.38–1.06 (18H, m), 0.89 (3H, br m);

MS: (M+23)m/z=922.

Example 5

Synthesis of peptide shown as LysProIleGluPhePhe (NO$_2$)-pNA.2CF$_3$COOH

By the same procedure as described in Example 2, the title compound having the following physical data was obtained.

$^1$H-NMR:(CD$_3$OD) δ=8.21 (2H, d), 8.14 (2H, d), 7.81 (2H, d), 7.52 (2H, d), 7.20–7.06 (5H, m), 4.61–4.50 (3H, m), 4.34 (1H, dd), 4.25 (1H, dd), 4.11 (1H, d), 3.72 (1H, br m), 3.58 (1H, br m), 3.14–2.84 (4H, m), 2.38–1.06 (18H, m), 0.89 (3H, t).

MS:(M+1)m/z=945.

Example 5 (a)

Synthesis of Peptide Shown as $N^{\alpha}$-AcLysProIleGlu-Phe($NO_2$)-Nle-pNA.$CF_3COOH$ By the same procedure as described in Example 1, the title compound having the following physical data was obtained.

$^1$H-NMR:($CD_3OD$) δ=8.21 (2H, d), 8.05 (2H, d), 7.83 (2H, d), 7.50 (2H, d), 4.74 (1H, dd), 4.58 (1H, dd), 4.45 (1H, dd), 4.42 (1H, dd), 4.34 (1H, dd), 4.08 (1H, d), 3.90–3.82 (1H, m), 3.68–3.60 (1H, m), 3.31 (2H, dd), 3.08 (2H, dd), 2.94 (2H, t), 2.33 (2H, t), 2.25–2.19 (1H, m), 2.10–1.24 (20H, m), 1.24–1.14 (1H, m), 0.92 (3H, t),0.88 (3H, t),0.82 (3H, d);

MALDI positive : (M+H)m/z=953,(M+Na)m/z=975,(M+K)m/z=991.

(2) Assay by Coloring p-NA

Enzyme solution I (0.1 ml) was added to Reagent (1.0 ml). After incubation of the mixture at 37° C. for 10 minutes, Enzyme solution II (0.05 ml) was added to the mixture solution (0.25 ml). After incubation of the mixture at 37° C. for 5 minutes, the increase in absorbance at 405 nm (Es) was determined. On the other hand, reagent blank value (E(BL)) was determined by the same procedure as above using purified water. According to the following, the increase in absorbance (E) was calculated.

$$E=Es-E(BL)$$

The results of assay by (1)HPLC and (2) coloring p-NA are shown in Table 1.

The ratio of pepsin I/pepsin II was calculated according to the result from assay by HPLC. Such assay is carried out to confirm that a substrate was digested by pepsin I or pepsin II correctly and that H-Y-pNA was released.

| Structure Formula (Example No.) | reaction pH | Quantity of pepsin (ng/ml) | Activitry of pepsin ($\mu$M/min · 909 ngEnz/ml) Determination by HPLC | | Activitry of pepsin (mABS/10 min · 909 ngEnz/ml) Determination by p-NA | | ratio of relative activity of |
|---|---|---|---|---|---|---|---|
| | | | pepsin I | pepsin II | pepsin I | pepsin II | pepsin I/pepsin II |
| $N^{\alpha}$-Ac-Lys-Pro-Ile-Glu-Phe-Nle-pNA.$CF_3COOH$ (Example 1) | 2.0 | 909 | 52.7 | 0.55 | 4391.7 | 45.8 | 95.8 |
| Lys-Pro-Ile-Glu-Phe-Nle-pNA.2$CF_3COOH$ (Example 2) | 3.0 | 909 | 8.6 | 0.37 | 716.7 | 30.8 | 23.2 |
| Lys-Pro-Ile-Glu-Phe-Tyr-pNA.2$CF_3COOH$ (Example 3) | 2.0 | 909 | 17.1 | 0.37 | 1425.0 | 30.8 | 46.2 |
| Lys-Pro-Ile-Glu-Phe-Phe-pNA.2$CF_3COOH$ (Example 4) | 3.0 | 909 | 10.9 | 0.16 | 908.3 | 13.3 | 68.1 |
| Lys-Pro-Ile-Glu-Phe-Phe($NO_2$)-pNA.2$CF_3COOH$ (Example 5) | 3.0 | 909 | 1.2 | 0.07 | 100.0 | 5.8 | 17.1 |
| $N^{\alpha}$Ac-Lys-Pro-Ile-Glu-Phe($NO_2$)-Nle-pNA.2$CF_3COOH$ (Example 5(a)) | 2.0 | 909 | 36.4 | 0.69 | 3036.2 | 57.3 | 52.8 |

Example 6

The Assaying Pepsin I and II on Digesting the Substrate of the Present Invention

[Reagent]

Formic acid buffer or glycine buffer (pH2.0~3.0) containing each peptide (0.5 mM) prepared in Example 1~5 (a)

[Enzyme Solution I]

An aqueous solution of human pepsin I or human pepsin II (0.01 mg/ml)

[Enzyme Solution]

Aminopeptidase M (marketed from Beringer Manheim Co., derived from pig kidney) was dissolved into 1M Tris-HCl buffer (pH9.0) to be at concentration of 2U/I.

[Method for Assay]

(1) Assay by HPLC

Enzyme solution I (0.1 ml) was added to Reagent (1.0 ml). After incubation of the mixture at 37° C. for 10, 30, 60 minutes, the mixture solution (0.3 ml) was collected. To the collected solution, 2N—NaOH (0.025 ml) was added to terminate the reaction. After addition of 2N—HCl (0.025 ml) to the mixture, protein was removed by the ultrafiltration. The assaying H-Y-pNA (Nle-pNA: Example 1 and 2; Tyr-pNA: Example 3; Phe-pNA: Example 4; Phe($NO_2$)-pNA: Example 5) which was released after digesting by human pepsin in the obtained solution was carried out by HPLC using C18 column.

As is shown clearly from the Table, we understand that a peptide of the present invention has the specificity for pepsin I. The result of the assay by coloring pNA shows similarly.

Example 7

The assaying human serum pepsinogen I by the method of the present invention (The correlation of the method between the present invention and RIA)

[Reagent Solution I]

$N^{\alpha}$-Ac-LysProIleGluPheNle-pNA.$CF_3COOH$ (prepared in Example 1) was dissolved into 50 mM tartaric acid buffer (pH2.0) to be at concentration of 0.5 mM.

[Reagent Solution II]

Aminopeptidase M (marketed from Beringer Manheim Co., derived from pig kidney) was dissolved into 0.8M Tris-HClbuffer (pH9.0) to be at concentration of 2U/I.

[Sample]

Thirty human serum samples

[Method for Assay]

Reagent solution I (0.25 ml) was added to sample (0.025 ml). After incubation of the mixture at 37° C. for 5 minutes, Reagent solution II (0.05 ml) was added thereto. After incubation of the mixture at 37° C. for 5 minutes, the increase in absorbance (Es) at 405 nm with reference at 600 nm was determined. On the other hand, reagent blank value (E(BL)) was determined by the same procedure as above using saline. According to the following, the increase in absorbance for 5 minutes (E) was calculated.

E=Es-E(BL)

Comparison

The assaying serum pepsinogen I was carried out by a marketed kit for assaying pepsinogen (Dinabott Co) (RIA method) according to the procedure described in explanation. The correlation of the results of the method between the present invention and RIA is shown in FIG. 1.

As is shown clearly from FIG. 1, we understand that there is a good correlation of the results of the method between the present invention and RIA, and that serum pepsinogen I was determined correctly by the method of the present invention.

What is claimed is:

1. A peptide substrate, or an acid addition salt thereof, wherein said peptide substrate is represented by formula (I)

$$\text{R-X-Pro-Ile-Glu-W-Y-Z} \qquad (1)$$

wherein
- R is a hydrogen, an amino-protective group, or a residue carrying one or two D- or L-amino acids,
- X is Lys or Arg,
- W is Phe or Phe(NO$_2$), wherein Phe(NO$_2$) is p-nitrophenylalanine,
- Y is Phe, Phe(NO$_2$), Tyr, Dit, Nle, Leu, Asp(Obzl) or Met, wherein Dit is 3,5-diiodotyrosine, Nle is norleucine, Obzl is benzyloxy, and Phe(NO$_2$) is p-nitrophenylalanine, and
- Z is an aniline derivative, an aminocoumarin derivative, or an aminonapthalene derivative.

2. The peptide substrate according to claim 1, wherein Y is Phe, Phe(NO$_2$), Tyr or Nle, and wherein Phe(NO$_2$) is p-nitrophenylalanine and Nle is norleucine.

3. The peptide substrate according to claim 1 or 2, wherein R is hydrogen or a C1–C6 alkylcarbonyl.

4. The peptide substrate, or an acid addition salt thereof, according to claim 1, selected from the group consisting of formulas (Ia), (Ib), (Ic), (Id), (Ie), and (If) as follows:

| | |
|---|---|
| Ac-Lys-Pro-Ile-Glu-Phe-Nle-pNA | (Ia) |
| Lys-Pro-Ile-Glu-Phe-Nle-pNA | (Ib) |
| Lys-Pro-Ile-Glu-Phe-Tyr-pNA | (Ic) |
| Lys-Pro-Ile-Glu-Phe-Phe-pNA | (Id) |
| Lys-Pro-Ile-Glu-Phe-Phe(NO$_2$)-pNA | (Ie) |
| Ac-Lys-Pro-Ile-Glu-Phe(NO$_2$)-Nle-pNA | (If) | wherein in said formulas,
- Ac is acetyl,
- Nle is norleucine, and
- pNA is p-nitroaniline.

5. A kit for assaying for the presence of human pepsin I, comprising:
  (a) a peptide substrate, or an acid addition salt thereof, wherein said peptide substrate is represented by formula (I)

$$\text{R-X-Pro-Ile-Glu-W-Y-Z} \qquad (I)$$

wherein
- R is a hydrogen, an amino-protective group, or a residue carrying one or two D- or L-amino acids,
- X is Lys or Arg,
- W is Phe or Phe(NO$_2$), wherein Phe(NO$_2$) is p-nitrophenylalanine, Y is Phe, Phe(NO$_2$), Tyr, Dit, Nle, Leu, Asp(Obzl) or Met, wherein Dit is 3,5-diiodotyrosine, Nle is norleucine, Obzl is benzyloxy, and Phe(NO$_2$) is p-nitrophenylalanine, and
- Z is an aniline derivative, an aminocoumarin derivative, or an aminonapthalene derivative, and (b) a aminopeptidase.

* * * * *

SEQUENCE LISTING

```
<160> NUMBER OF SEQ ID NOS: 7

<210> SEQ ID NO 1
<211> LENGTH: 8
<212> TYPE: PRT
<213> ORGANISM: Artificial Sequence
<220> FEATURE:
<223> OTHER INFORMATION: Description of Artificial  Sequence: synthetic
      peptide used for assaying purposes
<221> NAME/KEY: MOD_RES
<222> LOCATION: (1..2)
<223> OTHER INFORMATION: any amino acid
<221> NAME/KEY: MOD_RES
<222> LOCATION: (3)
<223> OTHER INFORMATION: Lys or Arg
<221> NAME/KEY: MOD_RES
<222> LOCATION: (7)
<223> OTHER INFORMATION: Phe or p-nitrophenylalani ne residue
<221> NAME/KEY: MOD_RES
<222> LOCATION: (8)
<223> OTHER INFORMATION: Phe, Tyr, Nle, Leu, Met, 3,5-diiodotyrosine,
      p-nitrophenylalanine or benzyloxyaspartic  acid, which
      is coupled to an aniline derivat ive, aminocoumarin
      derivative or aminonaphthalene derivat ive
<223> OTHER INFORMATION: This peptide may also encompass a sequence
      without residue one, residue two, or both.

<400> SEQUENCE: 1

Xaa Xaa Xaa Pro Ile Glu Phe Xaa
  1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial  Sequence: synthetic
      peptide used for assaying purposes
<221> NAME/KEY: MOD_RES
<222> LOCATION: (1)
<223> OTHER INFORMATION: N-alpha-acetyllysine residue
<221> NAME/KEY: MOD_RES
<222> LOCATION: (6)
<223> OTHER INFORMATION: p-nitroanilylnorleucine resi due

<400> SEQUENCE: 2

Lys Pro Ile Glu Phe Xaa
  1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial  Sequence: synthetic
      peptide used for assaying purposes
<221> NAME/KEY: MOD_RES
<222> LOCATION: (6)
<223> OTHER INFORMATION: p-nitroanilylnorleucine resi due
```

<400> SEQUENCE: 3

Lys Pro Ile Glu Phe Xaa
 1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial  Sequence: synthetic
      peptide used for assaying purposes
<221> NAME/KEY: MOD_RES
<222> LOCATION: (6)
<223> OTHER INFORMATION: p-nitroanilyltyrosine residu e

<400> SEQUENCE: 4

Lys Pro Ile Glu Phe Tyr
 1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial  Sequence: synthetic
      peptide used for assaying purposes
<221> NAME/KEY: MOD_RES
<222> LOCATION: (6)
<223> OTHER INFORMATION: p-nitroanilylphenylalanine r esidue

<400> SEQUENCE: 5

Lys Pro Ile Glu Phe Phe
 1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial  Sequence: synthetic
      peptide used for assaying purposes
<221> NAME/KEY: MOD_RES
<222> LOCATION: (6)
<223> OTHER INFORMATION: p-nitro(p-nitroanilyl)phenylala nine residue

<400> SEQUENCE: 6

Lys Pro Ile Glu Phe Phe
 1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial  Sequence: synthetic
      peptide used for assaying purposes
<221> NAME/KEY: MOD_RES
<222> LOCATION: (1)
<223> OTHER INFORMATION: N-alpha-acetyllysine residue
<221> NAME/KEY: MOD_RES
<222> LOCATION: (5)
<223> OTHER INFORMATION: p-nitrophenylalanine residue
<221> NAME/KEY: MOD_RES
<222> LOCATION: (6)

```
<223> OTHER INFORMATION: p-nitroanilylnorleucine residue

<400> SEQUENCE: 7

Lys Pro Ile Glu Phe Xaa
 1               5
```